United States Patent [19]

Szegö et al.

[11] Patent Number: 4,734,432

[45] Date of Patent: Mar. 29, 1988

[54] STABILIZED PLANT PROTECTING CARBOFURAN SUSPENSIONS

[75] Inventors: András Szegö; Viktória Péterdi; Ferenc Kováts; József Sós; István Rácz; Sándor Ángyán, all of Budapest; Katalin Mármarosi née Kellner, Biatorbágy, all of Hungary

[73] Assignee: Chinoin Gyogyszer- es Vegyeszeti Termekek Gyara R.T., Budapest, Hungary

[21] Appl. No.: 831,467

[22] Filed: Feb. 19, 1986

Related U.S. Application Data

[63] Continuation of Ser. No. 512,449, Jul. 11, 1983, abandoned.

[30] Foreign Application Priority Data

Jul. 9, 1982 [HU] Hungary ............... 2241/82

[51] Int. Cl.[4] ........................... A01N 43/08
[52] U.S. Cl. .................................. 514/469
[58] Field of Search .............. 514/469, 571; 71/92

[56] References Cited

U.S. PATENT DOCUMENTS 3,152,880 10/1964 Weed .................................. 71/92
3,474,170 10/1969 Scharpf ............................ 424/285

OTHER PUBLICATIONS

Chemical Abstracts; vol. 91, #51104y; Plant–Protective Concentrates; Kovats.

*Primary Examiner*—Albert T. Meyers
*Assistant Examiner*—Joseph A. Lipovsky
*Attorney, Agent, or Firm*—Karl F. Ross; Herbert Dubno; Jonathan Myers

[57] ABSTRACT

The present invention relates to a stabilized plant protecting agent suspension which can be characterized by containing 10 to 60% by weight of one or more active ingredients, 30 to 5% by weight of oily layer, 0 to 10% by weight of emulsifier, 10 to 20% by weight of conventionally used excipient and water needed to 100% by weight while by increasing solid concentration oil concentration decreases. The invention also provides a process for the preparation of a stabilized plant protecting agent suspension by adding oil and optionally an emulsifier and/or water containing layer to a suspension of a suitable particle size of the active ingredient and water soluble excipients, such as surfactants, optionally emulsifiers, dispersing agents, viscosity modifying agents, protective colloids and mixing together the suspension layer and the layer containing the oil with a stirrer of great shearing force and optionally adding to the obtained stabilized suspension further excipients, e.g. viscosity modifying agents, anti-foaming agent, protective colloid and dispersing agent.

5 Claims, No Drawings

STABILIZED PLANT PROTECTING CARBOFURAN SUSPENSIONS

This is a continuation of co-pending application Ser. No. 512,449, filed on July 11, 1983, now abandoned.

The present invention relates to a plant protecting agent suspension stabilized with an emulsion showing an outstanding stability during storing and improving the conditions of plant protecting activity.

It is known that spraying is the most often used method of application of plant protecting agents.

The effective amount of the active ingredient is dispersed in a liquid, preferably in water. Water insoluble active ingredients are sprayed in the form of a suspension after grinding to a suitably small particle size.

The preparation of the spray liquid needs thorough work and is the basis of economical and expert plant protection. The uniform distribution of the active ingredient in the spray liquid, and a constant concentration thereof are of great importance. To meet these requirements various wetting agents and/or dispersing agents are generally used. These excipients are partly added when producing the plant protecting agents, partly when preparing the spray liquid, the excipients are used as tank additives. As tank additives components increasing activity are also used. As such components various oils improving adherence of the active ingredients to plant parts and/or the absorption thereof GB-PS Na 1 190 6144 can be mentioned. Water insoluble plant protecting agents used in the form of spray can be formulated as so called wettable powders suitable for spray WP and as the so called stable suspensions FW. The latter are more and more used as they can be readily diluted without forming dust.

A difficulty arises, however, as the insoluble substances often sediment. The suspension stability of the compositions is promoted by various excipients. Apart from the water insoluble, well ground solid active ingredient the stable suspensions contain the following components:
dispersing agent
wetting agent
anti-freezing agent
agents ensuring meltableness consistence.

All these components are water soluble solid or liquid substances.

We have found that the detached standing and the floatability in water of the particles of the insoluble solid in aqueous suspension is increased by a water insoluble, but finely emulsified suitable liquid, i.e. this liquid improves the long-lasting stability of the plant protecting agent during storing or after a long storage.

A two-layer system is provided having at least three components characterized by consisting of a plant protecting agent in the solid layer a dispersed state and the second layer consisting of an emulsion having at least two components. The terms "layer" and "component" are defined as follows: The "layer" refers to "components" of a macroscopically different state, whereas a component defines a material quality. Emulsion characterized as a layer means of course a liquid system consisting of two liquids being inmiscible or limitedly miscible with each other, where one liquid is homogeneously dispersed in the other liquid in form of drops and thus the system can be macroscopically considered as one single layer.

Physical and physico-chemical properties are partly determined by the plant protecting agent formulation and partly by direct agricultural use. These properties can be measured by parameters and by rheological characteristics referring to the stability of the system.

We have found that the size distribution of the components of the layers is optimal when the size distribution of the layer dispersed in emulsion and of the solid layer are of the same order of magnitude, i.e. in an optimal case the average size is identical or approximately identical.

We have further found that if one uses oil, preferably paraffin oil as a water insoluble liquid increasing the stability of the suspoemulsion, one can experience the following advantages: the suspension stability of the plant protecting agent is increased, the adherence of the applied agent on the plant is improved accompanied by said advantageous activity of the paraffin oil. As oil therapeutical white oil may be employed.

The formulation is characterized by outstanding physical and physico-chemical stability. The application dosage can be determined with or without the addition of water.

The optimal size distribution of the disperse layer of the emulsion can be assured with a surfactant of suitable quality and amount and/or a machine with great shearing force can be used minimal peripheral speed 5 m/s. The special embodiments of the invention will be summarized in the Examples. The composition of a general suspoemulsion concentrate is as follows:

| | |
|---|---|
| active ingredient[s] | 10–60% by weight |
| oil[s] | 5–30% by weight |
| emulsifier[s] | 0–10% by weight |
| excipient[s] | 10–20% by weight |
| water | ad 100% by weight |

As active ingredients the following types may be employed:

Fungicides:

(a) non-systemic fungicides, such as dithiocarbamates, thiuram-sulfides such as Basfungin, Dithan 445, TMTD, N-trichloro-methyl-mercapto derivatives, such as phthalmide derivatives such as Captan, -sulfon amide derivatives such as Euparen, imidazole and guanidine derivatives, such as Dodin, aromatic nitriles, such as Delan, aromatic nitro compounds such as Botran, other non systemic organic fungicides, e.g. heterocycles containing chloroaniline substituent, inorganic fungicides containing sulphur or copper, such as Morestan.

(b) systemic fungicides:
benzimidazole derivatives e.g. benomyl, BCM,
anilides, e.g. Mebenyl,
pyrimidine derivatives e.g. Ethirimol,
morpholine derivatives e.g. Calixin,
piperazine derivatives e.g. Triforin,
phosphoric acid ester derivatives e.g. Pyrazophos,
Herbicides:
systemic translocating herbicides:
halogenated aliphatic acids e.g. Na-Ta,
phenoxy alkane carboxylic acids and derivatives thereof e.g. 2,4-D,
phenoxy ethanol derivatives e.g. 2,4-Des,
aromatic carboxylic acids and derivatives thereof e.g. Amiben, Bromoximil,
carbamates, e.g. TPC,
thiol carbamates e.g. EPTC, urea derivatives e.g. Chlorbromin, substituted pyridazones e.g. Pyrazon,
substituted uracil derivatives e.g. Venzar,
triazine derivatives.

Insecticides:
chlorinated hydrocarbons e.g. HCH,
phosphorus containing organic insecticides e.g. Etopropylphorat,
carbamate type organic insecticides,
carbamic acid esters e.g. Carbofuran, Dioxacarb,
other organic insecticides.

Chemical names of the active ingredients indicated above by commercial names:
Basfungin: ammonium complex of propylene bis-thiocarbamyl disulfide and zinc propylene-bis-dithiocarbamate
Dithane M-45: manganese zinc-ethylene-bis-dithiocarbamate,
TMTD: tetramethyl-tiuram-disulfide,
Captan: N-trichloro-methylthio-tetrahydro-phthalimide,
Euparen: N,N-dimethyl-N'-phenyl-N'-fluorodichloromethylthio-sulfamide,
Dodin: dodecyl-guanidin-acetate,
Delan: 1,4-dithio-anthraquinone-2,3-dicarbo-nitrile,
Botran: 2,6-dichloro-4-nitro-aniline,
Morestan: 6-methyl-quinoxaline-2,3-dithiol-cyclocarbonate,
Benomyl: 1-butylcarbamoyl-2-carbomethoxyamino-benzimidazole,
BCM: 2-carbomethoxy-amino-benzimidazole,
Mebenil: o-toluyl-anilidine,
Ethirimol: 5-n-butyl-2-ethyl-amino-6-hydroxy-4-methylpyrimidine,
Calixin: N-tridecyl-2,6-dimethyl-morpholine,
Triforin: N,N'-bis-formamido-2,2,2- trichloro-ethylpiperazine,
Pyrazophon: 2-O-O-diethyl-O-6-ethoxy-carbamoyl-5-methylpyrazolo- 2,3-a-pyrimidine-2,2-yl-phosphorthioate,
Na-Ta: sodium-trichlor-acetate,
2,4 D: 2,4-dichloro-phenoxy-acetic acid,
2,4-Des: 2,4-dichloro-phenoxy-ethyl-sodium-sulphate,
Amiben: 3-amino-2,5-dichloro-benzoic acid,
Bromoxynil: 3,5-dibromo-4-hydroxy-benzo-nitrile,
PFC: phenyl-carbamic acid-isopropyl-ester,
EPTC: S-ethyl-N,N-di-n-propyl-thiolcarbamate,
Chlorbromuron: N-4-bromo-3-chlorophenyl-N'-methoxy-N'-methyl-urea,
Pyrazon: 1-phenyl-4-amino-5-chloro-pyridazone-6
Vanzar: 3-cyclohexyl-5,6-trimethylene-uracyl,
Cianazin: 2-4-chloro-6-methyl-amino-s-triazine-2-yl-amino- 2-methyl-propionitrile,
HCH: 1,2,3,4,5,6-hexachloro-cyclohexane,
Profos or Etoprop: S,S-dipropyl-6-ethyl-dithio-phosphate,
Porat: O,O-diethyl-S-ethyl-thio-methyl-dithio-phosphate,
Carbofuran: 2,3-dihydro-2,2-dimethyl-7-benzofuranyl-methyl-carbamate,
Dioxacarb: 2-1,3-dioxolan-2-yl phenyl-N-methyl-carbamate.

We have unexpectedly found that in order to achieve same rheological parameters in the suspoemulsion systems prepared as given above the average particle size of the solid layers and the disperse part of the emulsion layer have to be of the same order of magnitude and that increasing solid concentration requires decreasing oil concentration.

Rheological identity is ensured by the solid layer having a concentration of 60% by weight and oil of 5% by weight or a solid concentration of 10% by weight and and oil concentration of 30% by weight. To a 10-60% by weight of the solid layer there is a linear relationship with an oil concentration of 30-5% by weight.

The suspension according to the invention can be prepared by adding oil or optionally a layer consisting of an emulsifier and/or water to a suspension of suitable particle size of the active ingredient and water soluble excipients, such as surfactants, optionally emulsifiers, dispersing agents, viscosity modifying agents, protective colloids and then admixing the layer containing the suspension and the oily layer by means of a mixer of great shearing force and adding, if desired, further excipients, such as viscosity modifying agents, anti-foaming agents, protective colloids, surfactants and dispersing agents to be obtained stabilized suspension.

The invention provides a method for the preparation of a suspoemulsion system having a better stability than the conventional products. The products according to the invention are suited to produce suspoemulsions prepared for agricultural use in spray and/or dressing and/or soil disinfection methods and which behave optimally.

The term "optimal" for a spraying method means a finely divided spray drop of limited evaporation, increased adherence, the biological activity being maximal, thus the required amount of the active ingredient can be reduced as the biologically active ingredient is strongly and permanently attached to the plant parts.

The term "optimal" in the dressing process means that the suspoemulsion can be well fitted to the application technology, as the plant protecting agent can be adhered to the thus dressed seeds without the danger of forming dust. Thus the suspoemulsion in an appropriate dosage makes dressing effective, the biological activity is increased together with a simultaneous elimination of phytotoxicity.

When disinfecting soil the term "optimal" means that the suspoemulsion can be applied to the soil together with combined soil disinfectants, fertilizers and herbicides, it increases the extent of surfacial distribution and improves the conditions of work due to its evaporation reducing effect.

The experimental tests prove that the suspension is unexpectedly stabilized by the oil applied in an emulsified state. The unexpected effect is shown hereinafter by using two known biologically active compositions without limiting the scope of our invention to said examples.

In the Examples the suspensions of the biologically active agents are compared by using a suspension with an oil emulsion layer increasing stability and a suspension without said oil emulsion.

Physico-chemical parameters of the suspension were determined directly after the preparation, then dividing same into three parts, loading them with heat at +20° C., at −10° C. and at +50° C. and then determined after one month. As the most important physico-chemical parameters the ones characterizing stabilization of the suspension and characterizing agricultural use were tested. The determination of floatability was performed by the standards CIPAC method 0.5% by weight of active ingredient in 250 ml standard hard water. The inclination to sedimentation is characterized by a "separation" and "deposit" state, the separation % was measured by filling 300 g. of the suspension to a glass vessel of a diameter of about 40 mm and a capacity of 500 ml. liquid which can be closed. The thickness of the layer not containing the solid layer was determined visually in the ratio of the height of the entire suspension. The term "deposit" means the appearance of the solid layer. In order to characterize the rheological properties the outflow time measured from a glass Ford No. 4 was given as viscosity characteristics.

The change of the particle size upon different heat production was monitored by means of 5 and 10 $\mu$m supersonic wet screening. In the Examples the active ingredient content of the given compositions was determined before and after heat loadings but the differences deviation were within the experimental scattering thus they do not figure among the evaluated data.

EXAMPLE 1

690 g. of Carbendazim aqueous suspension were used. [composition: 200 g. of 2-carbomethoxy-amino-benzimidazole, 27 g. of nonyl phenol-poly glycol ether formed with 20 moles ethylene oxide Tensilin 080, 58 g. of ammonium chloride and water]

To a suspension of 690 g. of Carbendazim an adduct of 16 g. of Ca-alkyl-aryl-sulfonate and non-ionic tenside Atlox 4868 B was mixed. In another vessel 198 g. of therapeutical white oil and 19 g. of alkyl aryl polyether-alcohol of HLB 10.4 Triton X-45 were dissolved and the mixture was stirred by means of a mixer of great shearing force at a peripheral speed of 15 m/s.

56 g. of ethylene glycol and 17 g. of water were admixed and in this mixture 2 g of polysaccharide Tensiofix 821 of anionic type were dissolved by a mixer of great shearing force and it was added to the above suspoemulsion. Foam was removed from the suspension with 2 g. of synthetic foam breaker Tensiofix L 051.

Physico-chemical tests mentioned above were conducted with the obtained suspension and the suspoemulsion was then divided to 3 equal parts for heat loading. After one month physico chemical parameters were measured again on samples stored at $-10°$ C., $+20°$ C. and $+50°$ C. The results are shown in Table 1.

EXAMPLE 2

One can proceed as disclosed in Example 1 referential Example but the solution of 198 g. of therapeutic white oil and 19 g. of alkyl aryl polyether alcohol of HLB 10.4 was replaced by 207 g. of water when preparing the suspension.

The tests were carried out according to Example 1. The results of Examples 1 and 2 are summarized in Table 1.

EXAMPLE 3

To a solution of 730 g. of water and 100 g. of glycerol 120 g. of Na-lignin sulfonate Borresperse N or Borresperse NA were added. In the obtained solution 800 g. of 2,3-dihydro-2,2-dimethyl-7-benzofuranyl-methylcarbamate further referred to as Carbofuran were suspended by means of a mixer of 20 m/s peripheral speed.

The suspension was filled to an atritor containing siliquarcit glass beads of a diameter of 1.5-1.2 mm. The wet grinding of the suspension was carried out for 1.5 hours at 710 min$^{-1}$ r.p.m. of the mixer. The glass beads were filtered off.

875 g. of the above suspension were separated and 30 g. of ethoxylal and hydrogenated castor oil Chremophor RH 60 were added. To the suspension a solution of 81 g. of therapeutic white oil and 9 g. of fat alcohol-polyglycolether Emulsogen M was added and homogenized for 2 minutes with the above stirrer of great shearing force.

To the thus obtained suspension 5 g. of polyvinylpyrolidone were added Plasdon K 25.

All physico-chemical and heat loading processes were performed with the suspension as given in Examples 1 and 2. The test results are summarized in Table 2.

TABLE 1

| Tested characteristics | After preparation | | After one month heat loading | | | | | |
|---|---|---|---|---|---|---|---|---|
| | | | at +20° C. | | at +50° C. | | at −10° C. | |
| | Example 3 | Example 4 | Example 3 | Example 4 | Example 3 | Example 4 | Example 3 | Example 4 |
| Separation % | 0 | 0 | 0 | 1.2 | 0 | 16.0 | 0 | 10.0 |
| Deposit % | 0 | 0 | 0 | 0 | 0 | 0 | 0 | 0 |

TABLE 2

| Tested characteristics | After preparation | | at +20° C. | | at +50° C. | | at −10° C. | |
|---|---|---|---|---|---|---|---|---|
| | Example 3 | Example 4 | Example 3 | Example 4 | Example 3 | Example 4 | Example 3 | Example 4 |
| Separation % | 0 | 0 | 1.0 | 25.0 | 1.0 | 12 | 5.6 | 9.2 |
| Deposit % | 0 | 0 | 0 | 0 | 0 | hard | 0 | hard |

EXAMPLE 4 (reference)

One proceeds as disclosed in Example 3 but the solution of 81 g. of therapeutical white oil and 9 g. of fat alcohol polyglycolether is replaced by 90 g. of water. The tests and heat loading processes were performed as given in the previous Examples. The comparison of the suspensions prepared in Example 3 and 4 are summarized in Table 2.

EXAMPLE 5

Biological activity of a fungicide with 20% Carbendazim as active ingredient, used as spray.

On 200 m$^2$ experimental fields "Berlin halflong" parsley was sprayed with a composition according to the invention against powdery mildew Erysiphe umbelliferarum.

The composition was applied at a rate of 600 l/ha. of spray liquid.

The infection percent and the infection index were determined after the treatments. The results are shown in Table 3.

TABLE 3

| Treatment | Dosage l/ha. | Infection % | Infection index $F_i$ |
|---|---|---|---|
| Fungicide of 20% active ingredient content [prepared according to Example 1] | 2.0 | 27.0 | 0.28 |
| Untreated control | — | 97.5 | 2.70 |

Infection index:

$$F_i = \frac{\Sigma a_i \cdot f_i}{m}$$

$F_i$ = infection index
$a_i$ = ratings
$f_i$ = frequency of the rating values
m = total number of the test plants

EXAMPLE 6

A fungicide with 20% by weight of Carbendazim active ingredient prepared according to Example 1 was used against Fusarium sp. diseases of maize at germination stage in the form of dressing agent.

Maize seeds infected innerly and externally with Fusarium in 29% were dressed with the fungicide prepared according to the invention. The activity against Fusarium sp. was evaluated in laboratory test and then free land experiments were carried out to evaluate the activity of some treatments.

The activity of the composition according to the invention was compared with highly active positive control fungicides.

| Treatment | Dosage kg./to. | Maize Fusarium infection % | Number of plants piece/m | Number of Sorghum piece/m |
|---|---|---|---|---|
| fungicide prepared according to Example 1 20% active ingredient | 3.0 | 3 | 7.5 | 8.3 |
| Orthocid 50 WP | 2.0 | 8 | 7.8 | 8.1 |
| Dithane M-45 | 2.0 | 3 | 7.5 | 8.42 |
| Buvishield K | 3.0 | 4 | 7.3 | — |
| untreated control | — | 29 | 6.2 | 6.5 |

Buvishield K is a fungicide dressing agent containing 30% by weight of Captane as active ingredient with increased adhesiveness.

EXAMPLE 7

Insecticidal composition prepared according to Example 3 containing 40% by weight of Carbofuran used as biological dressing agent.

Maize seeds were dressed with a composition containing as active ingredient 40% by weight of Carbofuran prepared as disclosed in Example 3.

The treated seeds were seeded with IHC seeding machine at a rate of 18.9 kg./ha. The effectiveness against wire worms Agriotes sp., fritflies Oscinella frit and plants louse was evaluated and the plant number in each running meter and the crop were measured. The results are shown in Table 4.

TABLE 4

| | Treatments | | |
|---|---|---|---|
| | Composition with 40% Carbofuran as active ingredient prepared as given in Example 3 | Chinufur 10 G* kg/ha | Untreated control |
| Wireworms piece/m² | | | |
| before treatment | 16.3 | 18.7 | 20.7 |
| after treatment | 5.0 | 4.3 | 18.8 |
| Infection with fritflies on the basis of 4 × 100 plants | 2.7 | 1.8 | 5.5 |
| Stems infected with plant louse on the basis of 4 × 100 plants | 1.1 | 2.1 | 9.0 |
| Number of plants in 10 m at 3 to 5 leaves age | 35.5 | 34.3 | 34.6 |
| Crop results kg/ha | 10200 | 9800 | 7340 |

Chinofur 6 is a granulate containing 10% by weight of carbofuran
*row treatment

EXAMPLE 8

Biological activity of a fungicide containing as active ingredient 40% by weight of Carbofuran prepared according to Example 3, application in the form of soil treatment.

The composition prepared as disclosed in Example 3 is tested in maize alone or combined with a herbicide or separately with a herbicide.

The composition was applied with a NOVOR 1005 spraying machine and it was worked into the soil with a disc adjusted to a deepness of 4 to 6 cm in an oblique angle. The effectiveness against wire worms was determined and the number of stems damaged by fritflies and corn weevil Tanymecus dilaticollis as well as the harvest were measured.

| Treatments | Dosage l/ha | Effectiveness against | | | Crop kg/ha |
|---|---|---|---|---|---|
| | | Wireworms | Fritflies | Corn weevil | |
| A | 5.0 | 83.3 | 83.0 | 77.2 | 7650 |
| Alirox 80 EC | 7.0 | — | — | — | 6710 |
| A + Alirox tank combination | 5.0 + 7.0 | 80.0 | 88.8 | 72.7 | 7010 |
| A + Alirox separately | " | 88.9 | 75.0 | 73.4 | 7050 |
| Chinufur 10 G | 20.0 | 94.4 | 83.3 | 81.2 | 7690 |
| Control | — | — | — | — | 6010 |

Alirox A 80 EC=preemergent herbicide containing 80% by weight of butylate
Chinufur 10 G=granulate containing 10% by weight of Carbofuran
A=composition containing 40% by weight of Carbofuran as given in Example 3.

We claim:
1. An insecticidal stabilized plant-protecting agent suspension which comprises:
   10 to 60% by weight of carbofuran;
   5 to 30% by weight of an oil phase;
   0 to 10% by weight of an emulsifier;
   10 to 20% by weight of an insecticidally inert carrier; and
balance water up to 100% by weight, and wherein the ratio of the carbofuran to the oil phase is linear between carbofuran:oil concentration ratio of 60%:5% and 10%:30% and the suspension is formed by high-shear mixing in a high-shear mixer rotating with a peripheral speed of 15 to 20 m/s.

2. The insecticidal composition defined in claim 1 wherein the oil phase comprises mineral oil, oil derived from animals, therapeutical white oil, soya oil, colza oil, sunflower oil, fish oil or paraffin oil.

3. A process for the preparation of an insecticidal, stabilized plant-protecting agent suspension which comprises:

10 to 60% by weight of carbofuran;
5 to 30% by weight of an oil phase;
0 to 10% by weight of an emulsifier;
10 to 20% by weight of an insecticidally inert carrier; and balance water up to 100% by weight, and wherein the ratio of the carbofuran to the oil phase is linear between carbofuran:oil concentration ratio of 60%:5% and 10%:30%, which comprises the steps of:

(a) adding an oil phase to a suspension of carbofuran to form an oil-containing layer and a suspension layer containing the carbofuran in a dispersed state; and (b) mixing together the suspension-layer and the oil-containing layer by means of a mixer having a peripheral speed of 15 to 20 m/s along with the carrier to obtain the stabilized suspension.

4. The process defined in claim 3 wherein an emulsifier, water, or both, are added to the suspension layer containing the carbofuran in a dispersed state.

5. The process defined in claim 3 wherein an emulsifier is added to the oil-containing layer.

* * * * *